United States Patent
Xie et al.

(10) Patent No.: US 11,304,679 B2
(45) Date of Patent: Apr. 19, 2022

(54) PHASE ABERRATION CORRECTION IN ULTRASOUND SHEAR WAVE ELASTOGRAPHY AND ASSOCIATED DEVICES, SYSTEMS, AND METHODS

(71) Applicant: KONINKLIJKE PHILIPS N.V., Eindhoven (NL)

(72) Inventors: Hua Xie, Cambridge, MA (US); Sheng-Wen Huang, Ossining, NY (US); Jean-Luc Francois-Marie Robert, Cambridge, MA (US); Man Nguyen, Melrose, MA (US); Vijay Thakur Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 508 days.

(21) Appl. No.: 16/331,185

(22) PCT Filed: Sep. 7, 2017

(86) PCT No.: PCT/EP2017/072493
§ 371 (c)(1),
(2) Date: Mar. 7, 2019

(87) PCT Pub. No.: WO2018/046611
PCT Pub. Date: Mar. 15, 2018

(65) Prior Publication Data
US 2019/0282209 A1    Sep. 19, 2019

Related U.S. Application Data

(60) Provisional application No. 62/536,099, filed on Jul. 24, 2017, provisional application No. 62/393,241, filed on Sep. 12, 2016.

(51) Int. Cl.
*A61B 8/08* (2006.01)
*G01S 7/52* (2006.01)

(52) U.S. Cl.
CPC .......... *A61B 8/485* (2013.01); *G01S 7/52042* (2013.01); *G01S 7/52049* (2013.01); *A61B 8/5215* (2013.01)

(58) Field of Classification Search
CPC .. A61B 8/485; G01S 7/52042; G01S 7/52049
See application file for complete search history.

(56) References Cited

U.S. PATENT DOCUMENTS 7,273,455 B2 * 9/2007 Angelsen ............ G01S 7/52038
600/437
10,722,215 B2    7/2020 Toji

OTHER PUBLICATIONS

Li, "Phase Aberration Correction Using Near-Field Signal Redundancy—Part I: Principles" IEEE Transactions on Ultrasonics, Ferroelectrics, and Frequency Control, vol. 44, No. 22, Mar. 1997 (Year: 1997).*

(Continued)

*Primary Examiner* — Colin T. Sakamoto

(57) ABSTRACT

Ultrasound image devices, systems, and methods are provided. In one embodiment, an ultrasound imaging system includes an interface coupled to an ultrasound imaging component and configured to receive a plurality of image data frames representative of a target tissue; and a processing component in communication with the interface and configured to determine a delay profile for the ultrasound imaging component in relation to the target tissue based on the plurality of image data frames; and determine a phase aberration correction configuration for a sequence of one or more shear wave pulses based on the delay profile, the sequence of one or more shear wave pulses associated with the ultrasound imaging component and a stiffness measure of the target tissue.

20 Claims, 5 Drawing Sheets

(56) References Cited

OTHER PUBLICATIONS

Nock et al., "Phase aberration correction in medical ultrasound using speckle brightness as a quality factor" The Journal of the Acoustical Society of America 85, 1819-1833, May 1989 (Year: 1989).*

Flax et al., "Phase-Aberration Correction Using Signals From Point Reflectors and Diffuse Scatterers: Basic Principles" IEEE Transactions on Ultrasonics, Ferroelectrics, and Frequency Control, vol. 35, No. 6, Nov. 1988 (Year: 1988).*

Michael Jaeger et al: "Full correction for spatially distributed speed-of-sound in echo ultrasound based on measuring aberration delays via transmit beam steering", Physics in Medicine and Biology, Institute of Physics Publishing, Bristol GB, vol. 60, No. 11, May 19, 2015 (May 19, 2015),pp. 4497-4515.

Amador Carrascal Carolina et al: "Phase Aberration and Attenuation Effects on Acoustic Radiation Force-Based Shear Wave Generation",IEEE Transactions on Ultrasonics, Ferroelectrics and Frequency Control, IEEE, US, vol. 63, No. 2, Feb. 1, 2016 (Feb. 1, 2016), pp. 222-232.

Huang Sheng-Wen et al: "Phase aberration in ultrasound shear wave elastography-impacts on push and tracking",2016 IEEE International Ultrasonics Symposium (IUS), IEEE, Sep. 18, 2016 (Sep. 18, 2016), pp. 1-4.

A. P. Sarvazyan et al ,"Shear wave elasticity imaging: A new ultrasonic technology of medical diagnostics," Ultrasound Med. Biol., vol. 24, No. 9, pp. 1419-1435, 1998.

Y. Shi et al "Phase aberration in shear wave dispersion ultrasound vibrometry," in Proc. IEEE Ultrason. Symp., pp. 2408-2411, 2011.

M. L. Palmeri et al "Quantifying hepatic shear modulus in vivo using acoustic radiation force," Ultrasound Med. Biol., vol. 34, No. 4, pp. 546-558, 2008.

C. Amador Carrascal et al "Phase aberration and attenuation effects on acoustic radiation force-based shear wave generation," IEEE Trans. Ultrason., Ferroelectr., Freq. Control, vol. 63, No. 2, pp. 222-232, 2016.

J. R. Doherty et al "Harmonic tracking of acoustic radiation force-induced displacements," IEEE Trans. Ultrason., Ferroelectr., Freq. Control, vol. 60, No. 11, pp. 2347-2358, 2013.

P. Song et al "Improved shear wave motion detection using pulse-inversion harmonic imaging with a phased array transducer," IEEE Trans. Med. Imag., vol. 32, No. 12, pp. 2299-2310, 2013.

M. Correia et al "Ultrafast harmonic coherent compound (UHCC) imaging for high frame rate echocardiography and shear-wave elastography," IEEE Trans. Ultrason., Ferroelectr., Freq. Control, vol. 63, No. 3, pp. 420-431, 2016.

C. Amador et al "Improvement of shear wave motion detection using harmonic imaging in healthy human liver," Ultrasound Med. Biol., vol. 42, No. 5, pp. 1031-1041, 2016.

M. O'Donnell and S. W. Flax "Phase-aberration correction using signals from point reflectors and diffuse scatterers: Basic principles," IEEE Trans. Ultrason., Ferroelectr., Freq. Control, vol. 35, No. 6, pp. 758-767, 1988.

C. Kasai et al, "Real-time two-dimensional blood flow imaging using an autocorrelation technique," IEEE Trans. Sonics Ultrason., vol. 32, No. 3, pp. 458-464, 1985.

M. Tanter, et al. "Quantitative assessment of breast lesion viscoelasticity: Initial clinical results using supersonic shear imaging," Ultrasound Med. Biol., vol. 34, No. 9, pp. 1373-1386, 2008.

* cited by examiner

PHASE ABERRATION CORRECTION IN ULTRASOUND SHEAR WAVE ELASTOGRAPHY AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2017/072493, filed on Sep. 7, 2017, which claims the benefit of U.S. Patent Application No. 62/536,099, filed on Jul. 24, 2017 and U.S. Patent Application No. 62/393,241, filed on Sep. 12, 2016. These applications are hereby incorporated by reference herein.

TECHNICAL FIELD

The present disclosure relates generally to ultrasound imaging and, in particular, to correcting phase aberration in ultrasound shear wave elastography (SWE) based on brightness-mode (B-mode) image data.

BACKGROUND

Ultrasound SWE is a non-invasive diagnostic tool for extracting quantitative tissue viscoelasticity information. Tissue stiffness may be indicative of certain diseases, for example, liver fibrosis. In addition, the degree or measure of the stiffness may be indicative of the severity of a disease, for example, staging the degree of liver fibrosis. In ultrasound SWE, an ultrasound imaging probe is used to produce shear waves in tissues and to measure the speed of the shear waves propagating through the tissues. For example, an ultrasound imaging probe may generate one or more push beams towards a target tissue to produce a shear wave at the target tissue followed by transmitting a series of tracking beams towards the target tissue. The ultrasound imaging probe may receive an echo sequence (e.g., receive tracking beams) reflected back from the target tissue. The displacements of the target tissue in response to the shear wave may be measured to estimate shear wave velocity based on the series of transmit and receive tracking beams. For example, a shear wave may travel at one velocity through a soft tissue, and at another, high velocity through a hard tissue. Thus, elasticity information or other mechanical characteristics of the target tissue can be obtained from the velocity measurements. Ultrasound SWE may be attractive for medical diagnosis due to the low cost and easy access of ultrasound imaging. In addition, ultrasound imaging can provide real-time image guidance for locating a region of interest.

However, a direct use of ultrasound for ultrasound SWE may provide limiting SWE performance due to phase and amplitude aberration, acoustic attenuation, clutter and reverberation effects of ultrasound imaging. For example, fat and muscle layers in near-field may pose a challenge to liver and abdominal scan. The fat and muscle layers may cause signal attenuation and phase aberration. Some studies have shown that phase aberration may degrade ultrasound SWE performance more than attenuation. For example, phase aberration can cause focusing errors in push beams and/or tracking beams. The focusing errors can lead to variations and errors in tissue stiffness measurements, and thus reproducing consistent, accurate stiffness measurements may be difficult. In addition, the focusing errors can potentially impact diagnosis outcomes and treatment options. Various studies attempted to improve ultrasound SWE performance, for example, by reducing the frequency of push beams or generating second harmonic signals non-linearly for tracking. However, such studies focus on reducing or minimizing ultrasound SWE performance degradation, rather than considering the underlying causes of the degradation.

SUMMARY

While existing ultrasound SWE has proved useful for determining tissue viscoelasticity, there remains a need for improved systems and techniques for improving ultrasound SWE performance. Embodiments of the present disclosure provide mechanisms for correcting phase aberration in ultrasound SWE based on B-mode image raw data. For example, an ultrasound imaging component can emit high-frame rate B-mode imaging pulses and low-frame rate shear wave pulses towards a target tissue in an interleaving manner shear wave pulses may include one or more push pulses followed by a series of tracking pulses. The underlying tissue acoustic characteristics that cause phase aberration can be estimated from echo responses of the B-mode imaging pulses. For example, an improved delay profile can be estimated for the ultrasound imaging component in relation to the target tissue based on the B-mode imaging echo responses. Phase aberration can be pre-compensated during the generation of subsequent push and/or tracking pulses in real-time or post-compensated during the reception of tracking echoes in real-time based on the estimated tissue acoustic characteristics. For example, beamforming delays can be computed for subsequent generation and/or reception of shear wave pulses based on the delay profile.

In one embodiment, an ultrasound imaging system is provided. The ultrasound imaging system includes an interface coupled to an ultrasound imaging component and configured to receive a plurality of image data frames representative of a target tissue; and a processing component in communication with the interface and configured to determine a delay profile for the ultrasound imaging component in relation to the target tissue based on the plurality of image data frames; and determine a phase aberration correction configuration for a sequence of one or more shear wave pulses based on the delay profile, the sequence of one or more shear wave pulses associated with the ultrasound imaging component and a stiffness measure of the target tissue.

In some embodiments, the plurality of image data frames include brightness-mode (B-mode) data from a plurality of channels, the plurality of channels corresponding to transducer elements of the ultrasound imaging component, and wherein the delay profile includes time-shift values for the plurality of channels. In some embodiments, the processing component is configured to determine the delay profile by determining a time-shift value for each of the plurality of channels to time-align the B-mode data across the plurality of channels. In some embodiments, the processing component is configured to determine the delay profile by selecting a subset of the B-mode data from each of the plurality of channels based on a spatial point of interest; and determining a time-shift value for each of the plurality of channels to time-align the subsets of the B-mode data across the plurality of channels. In some embodiments, the processing component is configured to determine the phase aberration correction configuration by determining beamforming delays for at least one of a generation or a reception of the sequence of one or more shear wave pulses by the transducer elements of the ultrasound imaging component. In some embodiments, the processing component is configured to determine a motion measure associated with the target tissue based on the plurality of image data frames; select a subset of the plurality of image data frames based on the motion measure; and determine the delay profile based on the subset of the plurality image data frames. In some embodiments, the sequence of one or more shear wave pulses includes at least one of a push pulse, a transmit tracking pulse, or a receive tracking pulse. In some embodiments, the interface is configured to transmit the phase aberration correction configuration to the ultrasound imaging component. In some embodiments, the interface is further configured to receive response data from the ultrasound imaging component, the response data associated with the sequence of one or more shear wave pulses in relation to the target tissue, and wherein the processing component is further configured to determine the stiffness measure of the target tissue based on at least the response data. In some embodiments, the ultrasound imaging system further comprises a display component in communication with the processing component and configured to display a confidence map associated with the stiffness measure of the target tissue. In some embodiments, the ultrasound imaging system further comprises a user input interface configured to receive a selection for an automatic phase aberration correction, wherein the processing component is configured to determine the phase aberration correction configuration based on the selection. In some embodiments, the ultrasound imaging system further comprises an ultrasound imaging probe including the ultrasound imaging component; the processing component; and a display component configured to display a confidence map associated with the stiffness measure of the target tissue.

In one embodiment, a method of ultrasound imaging diagnostic is provided. The method includes receiving, from an ultrasound imaging component, a plurality of image data frames representative of a target tissue; determining a delay profile for the ultrasound imaging component in relation to the target tissue based on the plurality of image data frames; and determining a phase aberration correction configuration for a sequence of one or more shear wave pulses based on the delay profile, the sequence of one or more shear wave pulses associated with the ultrasound imaging component and a stiffness measure of the target tissue.

In some embodiments, the plurality of image data frames include brightness-mode (B-mode) data from a plurality of channels, the plurality of channels corresponding to transducer elements of the ultrasound imaging component, and wherein the delay profile includes time-shift values for the plurality of channels. In some embodiments, the determining the delay profile includes determining a time-shift value for each of the plurality of channels to time-align the B-mode data across the plurality of channels. In some embodiments, the determining the delay profile includes selecting a subset of the B-mode data from each of the plurality of channels based on a spatial point of interest; and determining a time-shift value for each of the plurality of channels to time-align the subsets of the B-mode data across the plurality of channels. In some embodiments, the determining the phase aberration correction configuration includes determining beamforming delays for at least one of a generation or a reception of the sequence of one or more shear wave pulses by the transducer elements of the ultrasound imaging component, and wherein the method includes transmitting the phase aberration correction configuration to the ultrasound imaging component. In some embodiments, the method further comprises determining a motion measure associated with the target tissue based on the plurality of image data frames; selecting a subset of the plurality of image data frames based on the motion measure; and determining the delay profile based on the subset of the plurality image data frames. In some embodiments, the method further comprises receiving, from the ultrasound imaging component, response data associated with the sequence of one or more shear wave pulses in relation to the target tissue; and determining the stiffness measure of the target tissue based on at least the response data. In some embodiments, the method further comprises displaying a confidence map associated with the stiffness measure of the target tissue.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DESCRIPTION

Figure 1:
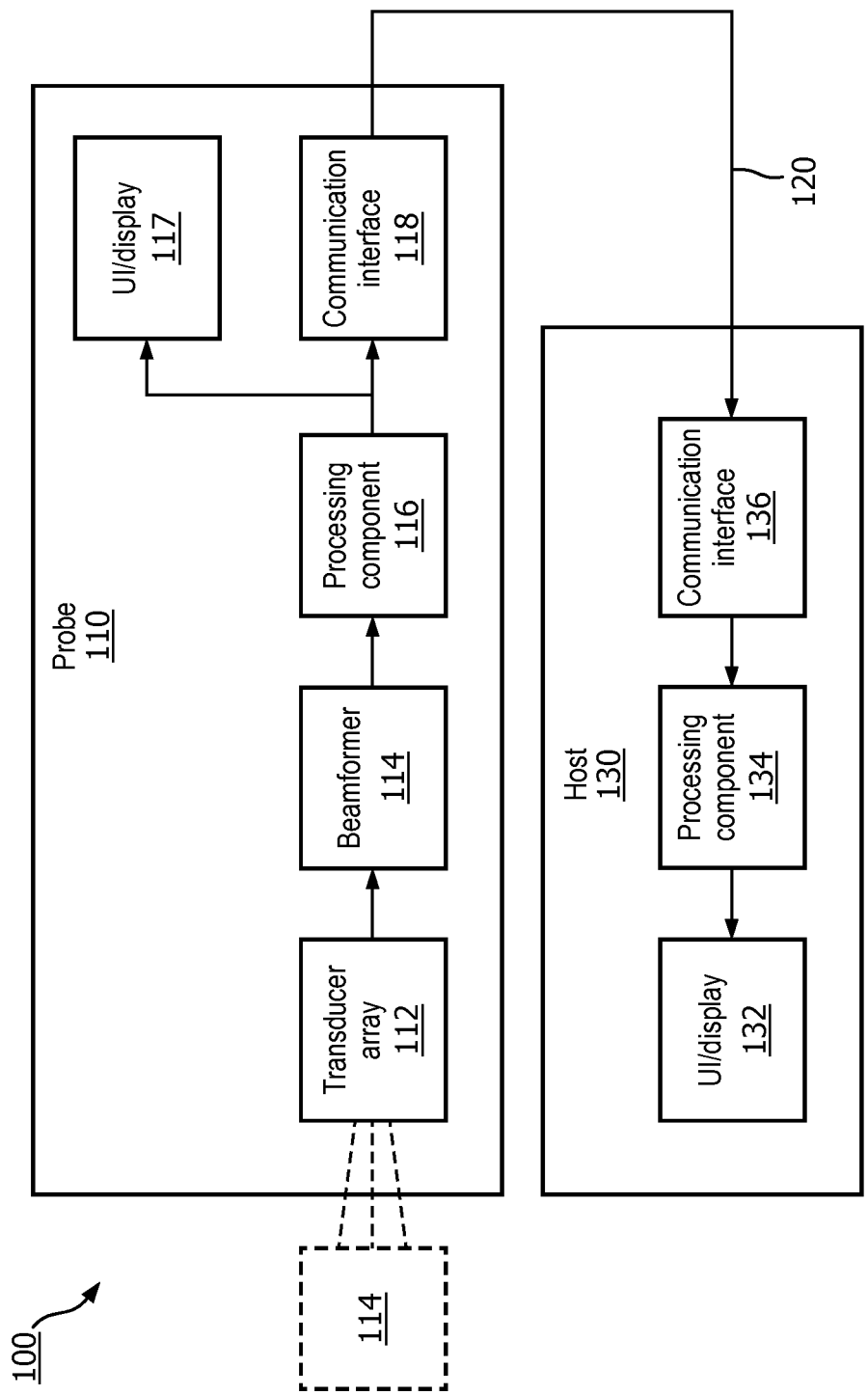
FIG. 1 is a schematic diagram of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an ultrasound imaging system 100, according to aspects of the present disclosure. The system 100 is used for scanning an area or volume of a patient's body. The system 100 includes an ultrasound imaging probe 110 in communication with a host 130 over a communication interface or link 120. The probe 110 includes a transducer array 112, a beamformer 114, a processing component 116, a UI/display unit 117, and a communication interface 118. The host 130 includes a UI/display unit 132, a communication interface 136, and a communication interface 136.

The transducer array 112 emits ultrasound signals towards an anatomical object 105 and receives echo signals reflected from the object 105 back to the transducer array 112. The transducer array 112 may include acoustic elements arranged in a one-dimensional (1D) array or in a two-dimensional (2D) array. The acoustic elements may be referred to as transducer elements.

The beamformer 114 is coupled to the transducer array 112. The beamformer 114 controls the transducer array 112, for example, for transmission of the ultrasound signals and reception of the ultrasound echo signals. The beamformer 114 provides image signals to the processing component 116 based on the response or the received ultrasound echo signals. The beamformer 114 may include multiple stages of beamforming. In an embodiment, the beamformer 114 is a delay and summing component configured to delay the transmission of ultrasound beams and/or the reception of echoes from the acoustic elements and to sum the reception of ultrasound echoes detected by the acoustic elements. In some embodiments, the transducer array 112 in combination with the beamformer 114 may be referred to as an ultrasound imaging component.

The processing component 116 is coupled to the beamformer 114. The processing component 116 generates image data from the image signals. The processing component 116 may be implemented as a combination of software components and hardware components. In an embodiment, the processing component 116 may be implemented on a field programmable gate array (FPGA) and may include programmable state machines to control the processing and conversion of the image signals to the image data. For example, the processing component 116 may perform filtering and/or quadrature demodulation to condition the image signals. The processing component 116 may perform analytic detection on the filtered signals. The UI/display unit 117 is coupled to the processing component 116. The UI/display unit 117 may include a screen, a touch-screen, or any suitable display or user-input components integral with the housing of the probe 110. The UI/display unit 117 may be configured to receive user inputs and/or display diagnostic results.

The communication interface 118 is coupled to the processing component 116. The communication interface 118 transmits the image signals to the host 130 via the communication link 120. At the host 130, the communication interface 136 may receive the image signals. The host 130 may be any suitable computing and display device, such as a workstation, a personal computer (PC), a laptop, a tablet, or a mobile phone. The communication link 120 may be any suitable communication link. For example, the communication link 120 may be a wired link, such as a universal serial bus (USB) link or an Ethernet link. Alternatively, the communication link 120 may be a wireless link, such as an ultra-wideband (UWB) link, an Institute of Electrical and Electronics Engineers (IEEE) 802.11 WiFi link, or a Bluetooth link.

The processing component 134 is coupled to the communication interface 136. The processing component 134 may be implemented as a combination of software components and hardware components. The processing component 134 may include a central processing unit (CPU), a digital signal processor (DSP), a graphical processing unit (GPU), an application-specific integrated circuit (ASIC), a controller, a field-programmable gate array (FPGA), another hardware device, a firmware device, or any combination thereof configured to perform the operations described herein. The processing component 134 may also be implemented as a combination of computing devices, e.g., a combination of a DSP and a microprocessor, a GPU and a microprocessor, a plurality of microprocessors, one or more microprocessors in conjunction with a DSP core, or any other such configuration. The processing component 134 can be configured to perform image processing and image analysis for various diagnostic modalities. The UI/display unit 132 is coupled to the processing component 134. The UI/display unit 132 may include a monitor, a touch-screen, a keyboard, a mouse, or any suitable display and user-input components. The UI/display unit 132 is configured to receive user inputs and/or display images and/or diagnostic results processed by the processing component 134.

The system 100 can be configured for ultrasound SWE. For example, the object 105 may correspond to a tissue structure (e.g., a liver) in a patient body. The transducer array 112 can be configured to generate brightness-mode (B-mode) pulses for B-mode imaging. In addition, the transducer array 112 can be configured to generate push pulses for shear wave generation and to generate and receive tracking pulses for shear wave propagation measurements. In an embodiment, the transducer array 112 is configured to generate B-mode imaging pulses interleaved with shear wave pulses (e.g., the push and tracking pulses). The echo responses from the B-mode imaging pulses can be used to calibrate or determine an ultrasound SWE phase aberration correction configuration (e.g., including beamforming delays or coefficients) for beamforming shear wave pulses transmitted and/or received by the acoustic elements of the transducer array 112. The transducer array 112 may be configured to generate and/or receive the shear wave pulses based on the phase aberration correction configuration. Thus, the system 100 can generate phase aberration corrected or aberration-free shear wave pulses in real time. Mechanisms for correcting phase aberration in ultrasound SWE are described in greater detail herein.

In some embodiments, the communication interface 118 can transmit B-mode image data to the host 130 via the link 120. At the host 130, the processing component 134 can determine a phase aberration correction configuration for beamforming shear wave pulses. The phase aberration correction configuration may include beamforming delays. The communication interface 136 can transmit the phase aberration correction configuration to the probe 110. The beamformer 114 can apply the beamforming delays to subsequent push pulses, transmit tracking pulses, and/or receive tracking pulses. Subsequently, the processing component 134 may determine tissue motion or displacement indicative of tissue elasticity or stiffness by monitoring the receive tracking pulses received from the probe 110. In some other embodiments, the determination of the beamforming delays can be performed at the processing component 116 of the probe 110 instead of at the host 130. In some other embodiments, the determination of the beamforming delays may be jointly performed by the processing component 116 of the probe and the processing component 134 of the host.

Figure 2:
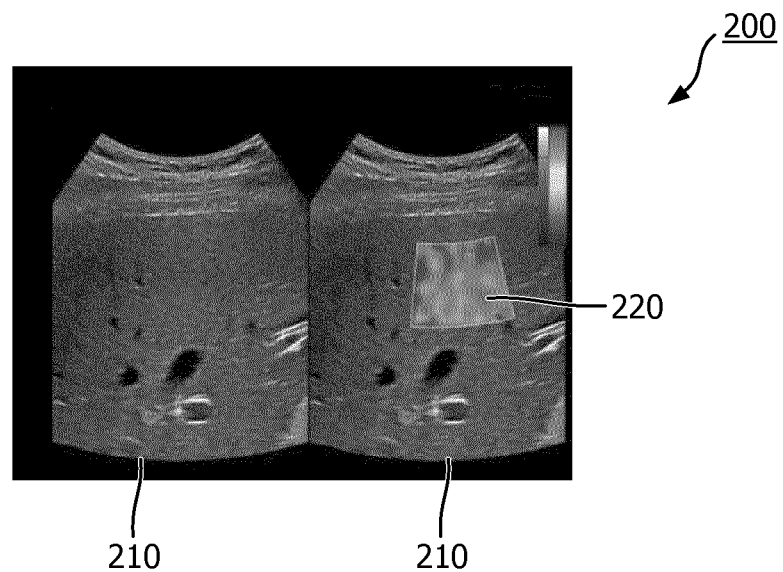
FIG. 2 illustrates an ultrasound shear wave elastography (SWE) imaging view, according to aspects of the present disclosure.

FIG. 2 illustrates an ultrasound SWE imaging view 200, according to aspects of the present disclosure. For example, the system 100 may be used to produce the imaging view 200. The imaging view 200 shows a B-mode image 210 of a fibrotic liver on the left side of the imaging view 200 and a shear wave stiffness map 220 superimposed on the B-mode image 210 on the right side of the imaging view 200. The B-mode image 210 is generated at a frame rate of about 65

Hertz (Hz). The shear wave stiffness map 220 is generated at a frame rate of about 0.5 Hz. Typically, SWE frame rate may be on an order of about 1 Hz, limited by Food and Drug Administration (FDA)-approved diagnostic ultrasound levels, whereas B-mode imaging frame rate may range between about 20 Hz to about 50 Hz. The shear wave stiffness map 220 indicates tissue stiffness measures or shear wave velocity measures. In some embodiments, the shear wave stiffness map 220 can be color-coded to indicate regions with different tissue stiffness measures or different velocities to assist a sonographer to locate a region of interest (ROI) or highlight regions with potential tissue stiffness issues. In some embodiments, the imaging view 200 can include a confidence map indicating the quality or the reliability of the stiffness measurements in the shear wave stiffness map 220, allowing a sonographer to obtain measurements from high-quality portions (e.g., pixels or sub-regions) of the shear wave stiffness map 220.

Figure 3:
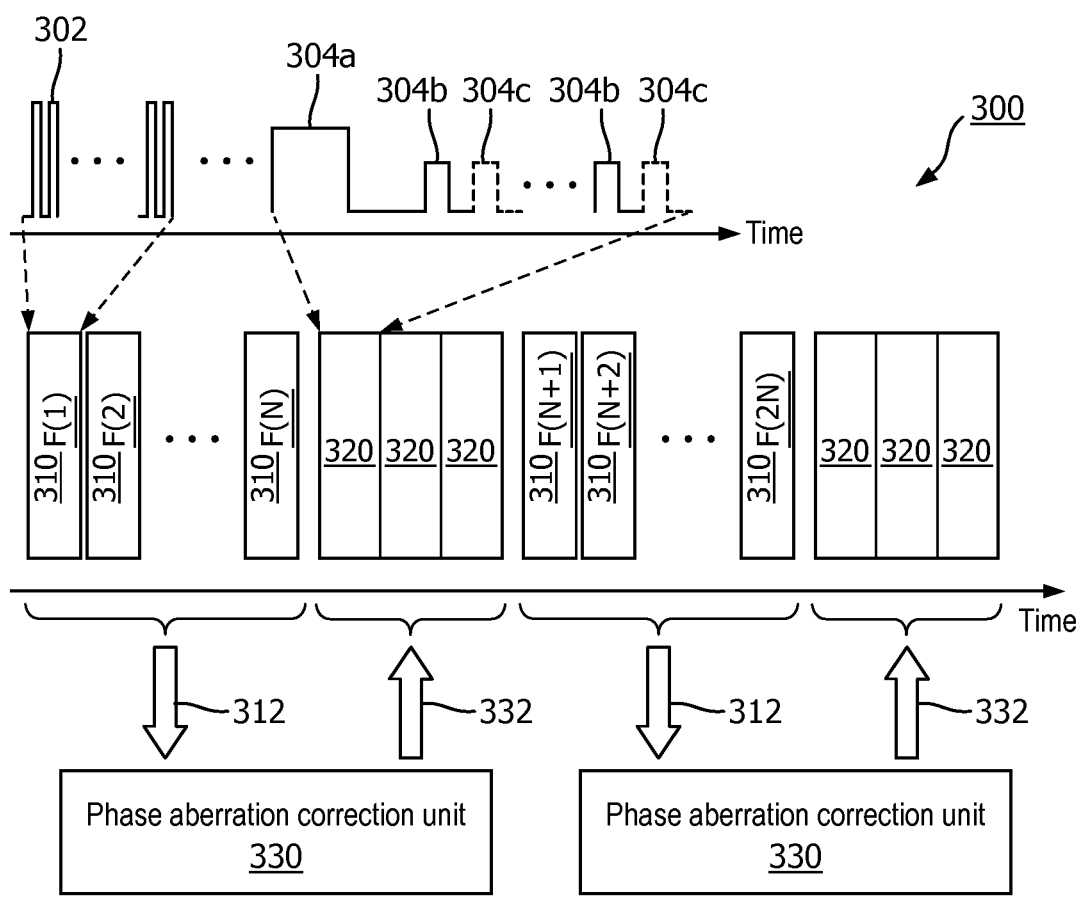
FIG. 3 is a schematic diagram illustrating a phase aberration correction scheme for ultrasound SWE, according to aspects of the present disclosure.
Figure 4:
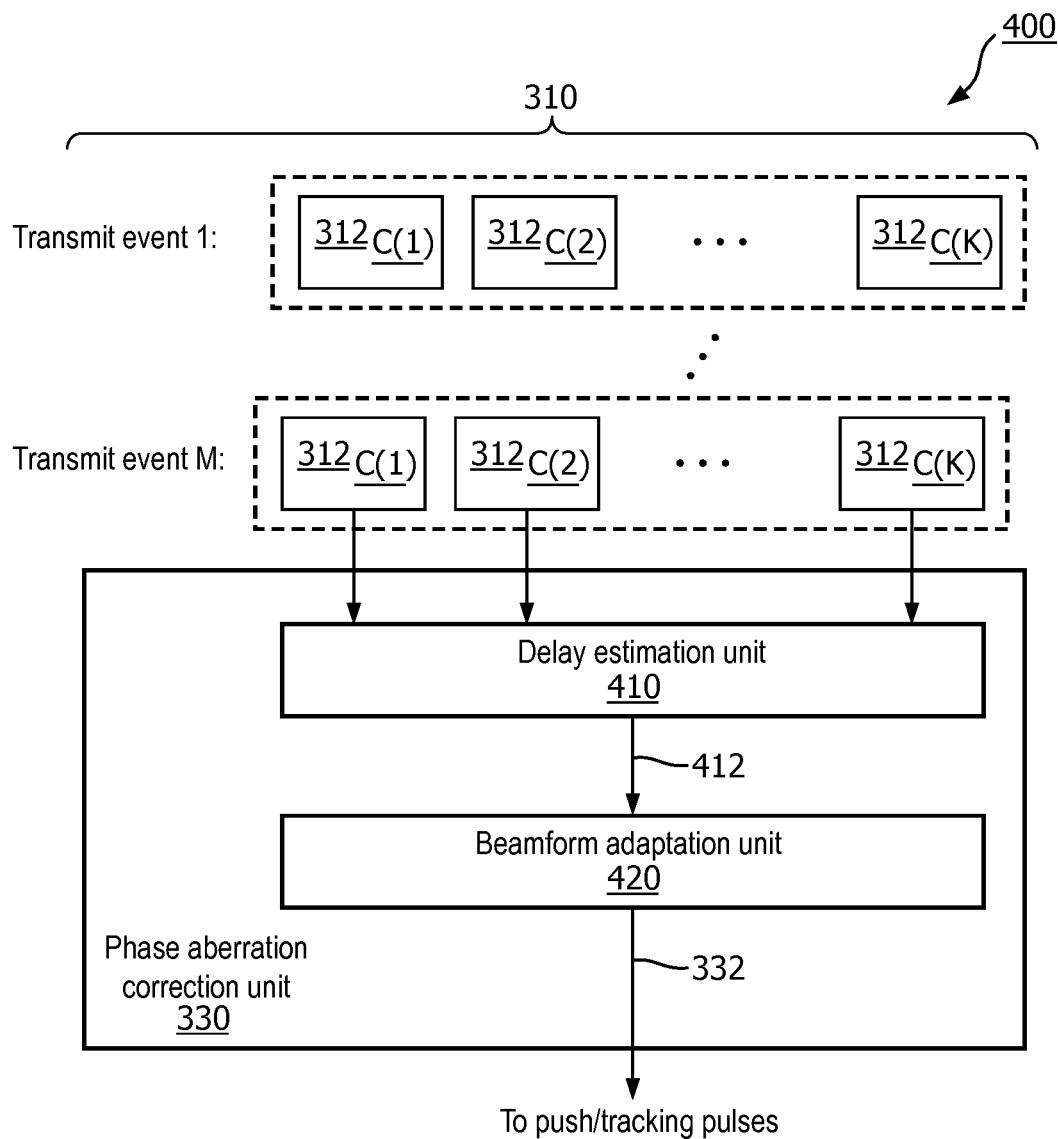
FIG. 4 is a schematic diagram illustrating a phase aberration correction scheme for ultrasound SWE, according to aspects of the present disclosure.
Figure 5:
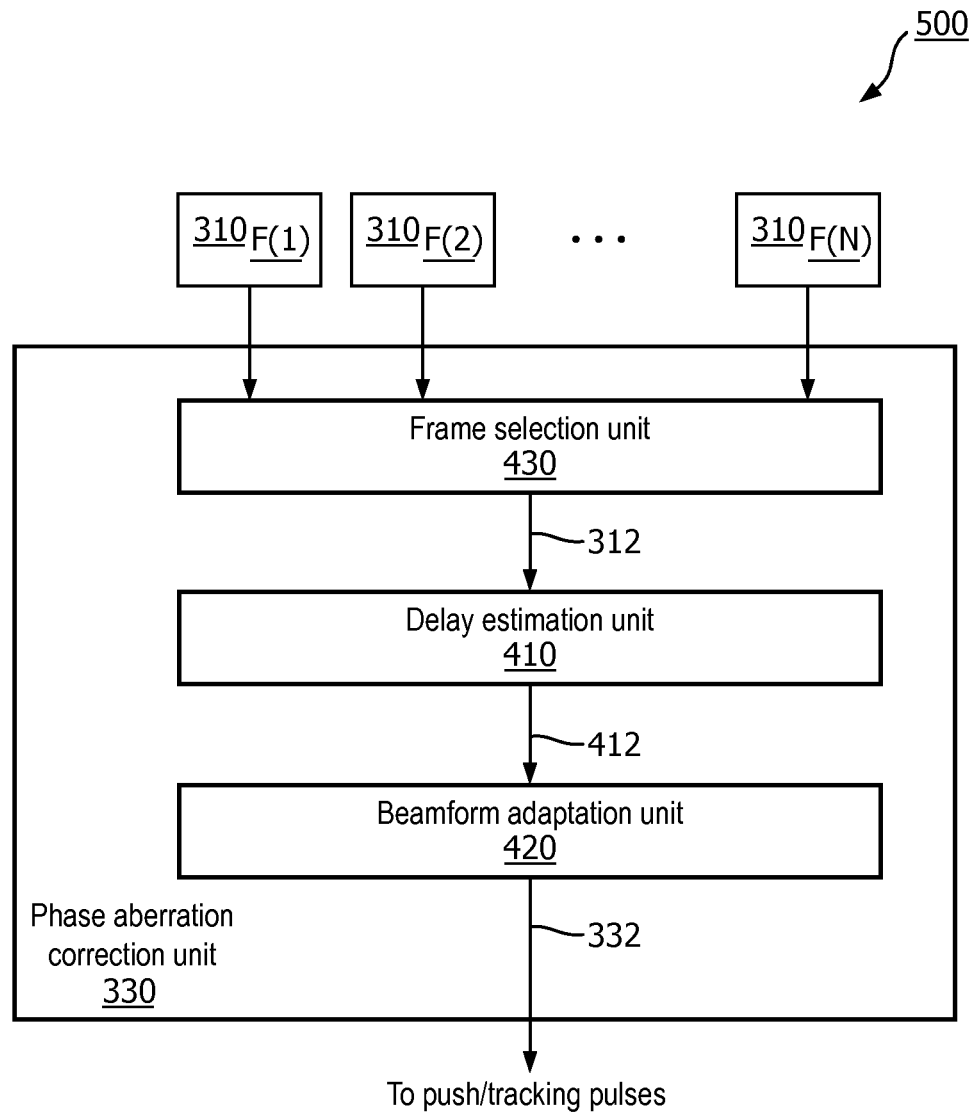
FIG. 5 is a schematic diagram illustrating a phase aberration correction scheme for ultrasound SWE, according to aspects of the present disclosure.

FIGS. 3-5 illustrate mechanisms for compensating phase aberration in ultrasound SWE. FIG. 3 is a schematic diagram illustrating a phase aberration correction scheme 300 for ultrasound SWE, according to aspects of the present disclosure. In FIG. 3, the x-axes represent time in some consumer units. The scheme 300 can be employed by the system 100 to correct phase aberration in ultrasound SWE. For example, the scheme 300 can be implemented by the processing component 134 on the host 130 or the processing component 116 on the probe 110. In some embodiments, the implementation of the scheme 300 can be divided between the host 130 and the probe 110.

The scheme 300 generates a sequence of B-mode imaging pulses 302 and a sequence of shear wave pulses 304 in an interleaving manner, for example, using an ultrasound transducer array such as the transducer array 112. The B-mode imaging pulses 302 and the shear wave pulses 304 may be emitted towards a target tissue such as the object 105. The transducer array may receive echo responses (not shown) of the B-mode imaging pulses 302 reflected from the target tissue. The echo responses of the B-mode imaging pulses 302 form image data frames 310. For example, each image data frame 310 may include a plurality of pixel values (e.g., amplitudes) representing pixel intensities of an image of the object 105. The image data frames 310 may have a high frame rate of about 20 Hz to about 50 Hz.

The shear wave pulses 304 may include one or more push pulses 304a followed by a series of transmit tracking pulses 304b. The push pulse 304a causes a shear wave generation at the object 105. The transducer array may receive echo responses (e.g., receive tracking pulses 304c) reflected from the target tissue in response to the transmit tracking pulses 304b.

The scheme 300 employs a phase aberration correction unit 330 to correct or compensate phase aberration in the generation and/or reception of the shear wave pulses 304. The phase aberration correction unit 330 receives B-mode data 312 of the image data frames 310. The phase aberration correction unit 330 determines a phase aberration correction configuration 332 for a subsequent acquisition sequence of shear wave pulses 304 based on the data 312. The high-frame rate B-mode image data frames 310 can provide an accurate estimates of the underlying tissue acoustic characteristics (e.g., fat and/or muscles between the transducer array 112 and the target tissue). The phase aberration correction configuration 332 is used to beamform the shear wave pulses 304. In an embodiment, the scheme 300 may apply the phase aberration correction configuration 332 to a beamformer (e.g., the beamformer 114) for generating and/or receive shear wave pulses 304.

The tracking echo responses (e.g., the receive tracking pulses 304c) form SWE data frames 320. The SWE data frames 320 may occur at a frame rate of about 0.5 Hz to about 1 Hz. Since the phase aberration correction unit 330 compensates phase aberration in the generation and/or reception of the shear wave pulses 304, the SWE data frames 320 includes phase aberration-free SWE data. For example, tissue displacements may be computed from the aberration-free data. Since tissue movements or displacements are representative of tissue stiffness, per-pixel stiffness measurements can be computed for the target tissue. By tracking tissue displacements at multiple locations along the shear wave propagation path, the shear wave velocity can be estimated and the absolute value of tissue mechanical properties can be determined. The shear wave velocity can be estimated base on various approaches, for example, time-to-peak based and cross-correlation based time-of-flight approaches and a wave equation approach.

While the scheme 300 illustrates N frames (e.g., shown as $310_{F(1)}$ to $310_{F(N)}$ of image data frames 310 interleaved with three SWE data frames 320, the scheme 300 can be applied to interleave N frames of image data frames 310 with any suitable number of SWE data frames 320 for ultrasound SWE phase aberration correction. In addition, the scheme 300 may vary the number of image data frames 310 in a sequence. For example, the first sequence may include N number of image data frames 310 and a subsequent sequence may include M number of image data frames 310.

FIG. 4 is a schematic diagram illustrating a phase aberration correction scheme 400 for ultrasound SWE, according to aspects of the present disclosure. The scheme 400 is similar to the scheme 300. The scheme 400 provides a more detailed view of the phase aberration correction in the scheme 300. As shown in FIG. 4, the phase aberration correction unit 330 includes a delay estimation unit 410 and a beamform adaptation unit 420.

In the scheme 400, the delay estimation unit 410 analyzes the radio frequency (RF) data 312 on a channel-by-channel basis. The data 312 corresponds to echo responses of the B-mode imaging pulses 302. The channels may correspond to acoustic elements of the transducer array 112. For example, when the transducer array 112 is configured to trigger K number of acoustic elements for transmission in a particular transmission event, the image data frames 310 may include data from the K receive channels. The data 312 from the K channels are shown as $312_{C(1)}$ to $312_{C(K)}$ for each transmit event indexed from 1 to M. Thus, each channel may correspond to a particular acoustic element. In some other embodiments, a channel may correspond to a subset of acoustic elements.

The delay estimation unit 410 is configured to determine a delay profile 412 for the transducer array 112 in relation to the target tissue. The delay estimation unit 410 may estimate time shifts to and from each individual acoustic element caused by phase aberration based on the per-channel data 312. In some embodiments, the delay estimation unit 410 may apply focusing delays to the per-channel data 312 according to a nominal acoustic wave travelling speed before determining the time-shifts.

In an embodiment, the delay estimation unit 410 may determine a single delay profile 412 for the K channels. In other words, a single delay profile is estimated for all pixels in the image data frames 310 or all transmission events associated with the image data frames 310. In such an embodiment, the delay estimation unit 410 may compute a time-shift value for each channel to time-align the data 312 across the K channels, for example, by computing cross-correlations across the per-channel data 312 and finding a maximum cross-correlation across the K channels.

In an embodiment, the delay estimation unit 410 may determine pixel-dependent delay profiles 412 for the K channels. In such an embodiment, the delay estimation unit 410 may estimate each delay profile 412 using per-channel data 312 around a corresponding point of interest (e.g., a particular spatial point or at a particular depth). For example, the delay estimation unit 410 may select a segment or a subset of the data 312 for each channel based on a particular point of interest and may compute a time-shift value for each channel to time-align the subsets across the K channels. The delay estimation unit 410 may repeat the subset selection and time-alignment for another point of interest.

The beamform adaptation unit 420 is configured to receive one or more delay profiles 412 and determine a phase aberration correction configuration 332 for the shear wave pulses 304 since the transmit and receive aperture configurations of the shear wave mode may be different from those of the B-mode. For example, the beamform adaptation unit 420 may determine beamforming delays for the acoustic elements of the transducer array based on the delay profiles 412 such that aberration-free SWE data may be obtained. The phase aberration correction configuration 332 may include the beamforming delays. In some embodiments, the beamform adaptation unit 420 may determine the beamforming delays or beamforming coefficients based on other criteria instead of the delay profiles 412. For example, the beamform adaptation unit 420 may determine beamforming coefficients based on a statistical metric, such as a minimum beamforming variance, that suppresses undesirable effects, such as clutters. The beamform adaptation unit 420 can also track or correlate the per-channel data 312 and the shear wave pulses 304 to avoid beamforming-induced decorrelation that can impact tissue motion tracking.

In an embodiment, the beamforming delays may be applied to the push pulses 304a to pre-compensate phase aberration. In an embodiment, the beamforming delays may be applied to the transmit tracking pulses 304b to pre-compensate phase aberration. In an embodiment, the beamforming delays may be applied to the receive tracking pulses 304c to post-compensate phase aberration. In some embodiments, the beamforming delays may be applied to any combination of the push pulses 304a, transmit tracking pulses 304b, and receive tracking pulses 304c to produce aberration-free SWE data frames 320.

FIG. 5 is a schematic diagram illustrating a phase aberration correction scheme 500 for ultrasound SWE, according to aspects of the present disclosure. The scheme 500 is similar to the schemes 300 and 400, but employs an additional frame selection unit 430. For example, the frame selection unit 430 can be configured to estimate a displacement of the target tissue and select image data frames 310 for delay estimation. When the tissue displacement is large, the frame selection unit 430 may select an image data frame 310 that is later in time (e.g., the image data frame $310_{F(N)}$ or $310_{F(2N)}$ close to the shear wave pulses 304, as shown in FIG. 3). The image data frame 310 later in time may be better aligned spatially with a subsequent sequence of shear wave pulses 304, and thus may provide more robust aberration suppression. When the tissue displacement is small, the frame selection unit 430 may select an image data frame 310 earlier in time (e.g., the image data frame $310_{F(1)}$ or $310_{F(N+1)}$ close to the shear wave pulses 304). When there is no tissue displacement, the frame selection unit 430 may select multiple image data frames 310 for better statistics Alternatively, the frame selection unit 430 may select image data frames based on the processing power of a processing component, such as the processing components 116 and 134. For example, the frame selection unit 430 may select an image data frame 310 earlier in time when the processing power is low to provide a sufficient amount of time for the delay estimation. The frame selection unit 430 may select one image data frame 310 or multiple image data frames 310 for delay estimation depending on the processing power.

While the schemes 300, 400, and 500 illustrate phase aberration correction to shear wave pulses 304, the phase aberration correction can also be applied to the B-mode imaging pulses 302. For example, a phase aberration correction configuration 332 estimated from the image data frames $310_{F(1)}$ or $310_{F(N)}$ can be used to beamform subsequent shear wave pulses 304 and subsequent B-mode imaging pulses 302 corresponding to image data frames $310_{F(N+1)}$ to $310_{F(2N)}$.

Figure 6:
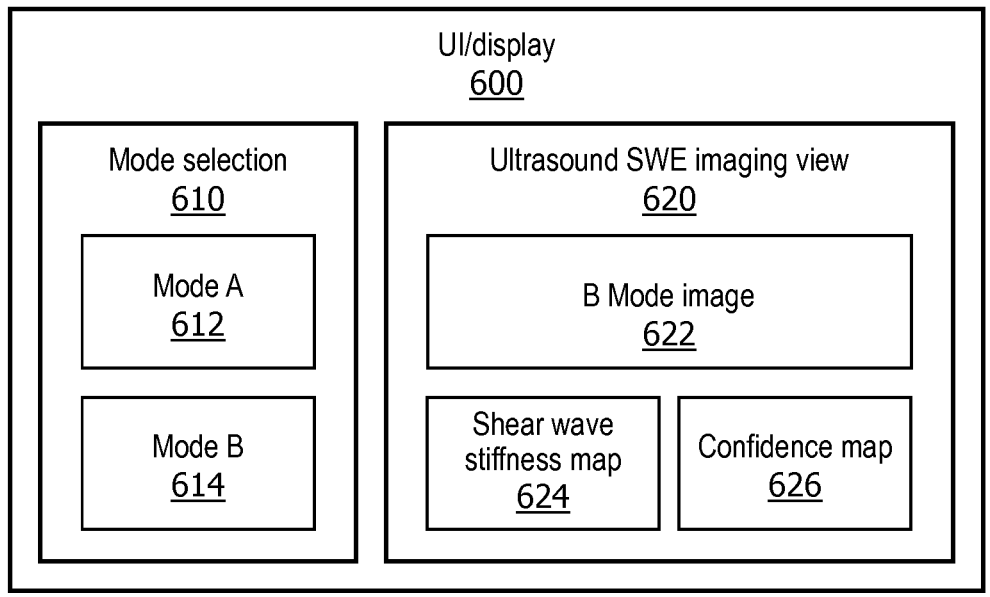
FIG. 6 is a schematic diagram of a user interface (UI)/display unit for ultrasound SWE, according to aspects of the present disclosure.

FIG. 6 is a schematic diagram of a UI/display unit 600 for ultrasound SWE, according to aspects of the present disclosure. The UI/display unit 600 may be employed by the system 100 for displaying ultrasound SWE results and/or receiving user inputs for controlling ultrasound SWE. For example, the UI/display unit 600 may represent the UI/display unit 117 or the UI/display unit 132. The UI/display unit 600 includes a mode selection unit 610 and an ultrasound SWE imaging view unit 620. The mode selection unit 610 may include user inputs configured to allow a user to select a mode A 612 or a mode B 614. For example, the mode A 612 may correspond to ultrasound SWE without phase aberration correction and the mode B 614 may correspond to ultrasound SWE with an automatic phase aberration correction similar to the schemes 300, 400, and 500 described above with respect to FIGS. 3, 4, and 5, respectively.

The ultrasound SWE imaging view unit 620 may display a B-mode image 622, a shear wave stiffness map 624, and a confidence map 626. The B-mode image 622 may be similar to the B-mode image 210 and may be generated from the B-mode image data frames similar to the B-mode image data frames 310. The shear wave stiffness map 624 may be similar to the shear wave stiffness map 220 and may be generated from SWE data frames similar to the SWE data frames 320. The shear wave stiffness map 220 may be a two-dimensional (2D) map including per-pixel stiffness measurements. The confidence map 626 may be a 2D map indicating per-pixel confidence level or quality of the stiffness measurements in the shear wave stiffness map 220 and may be generated based on a signal-to-noise (SNR) of corresponding shear wave pulses.

In some embodiments, the ultrasound SWE imaging view unit 620 may superimpose the shear wave stiffness map 624 and/or the confidence map 626 with the B-mode image 622. In some embodiments, the ultrasound SWE imaging view unit 620 may display a confidence map 626 without phase aberration correction and a confidence map 626 with the phase aberration correction. A sonographer can assess the quality of the stiffness measurements for both modes and select the mode A 612 or the mode B 614 based on the assessment.

Figure 7:
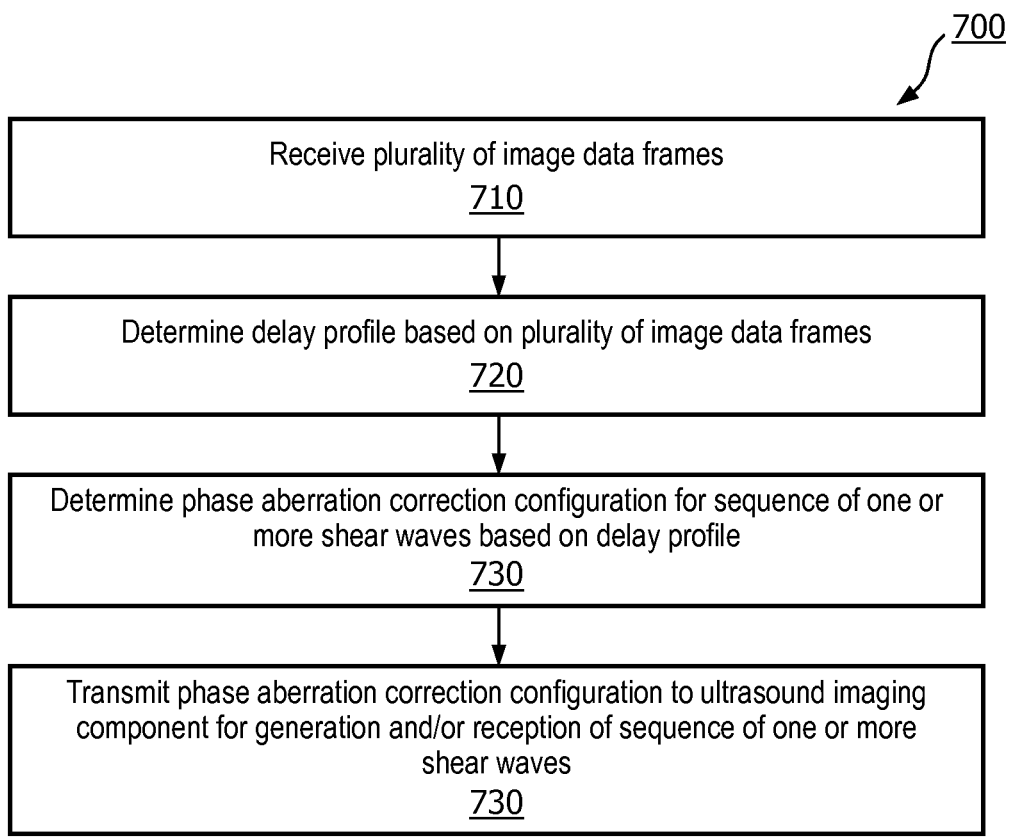
FIG. 7 is a flow diagram of a phase aberration correction method for ultrasound SWE, according to aspects of the present disclosure.

FIG. 7 is a flow diagram of a phase aberration correction method 700 for ultrasound SWE, according to aspects of the present disclosure. Steps of the method 700 can be executed by a computing device (e.g., a processor, processing circuit, and/or other suitable component) of an ultrasound imaging probe, such as the probe 110, or a host such as the host 130. The method 700 may employ similar mechanisms as in the schemes 300, 400, and 500 as described with respect to FIGS. 3, 4, and 5, respectively. As illustrated, the method 700 includes a number of enumerated steps, but embodiments of the method 700 may include additional steps before, after, and in between the enumerated steps. In some embodiments, one or more of the enumerated steps may be omitted or performed in a different order.

At step 710, the method 700 includes receiving a plurality of image data frames (e.g., the image data frames 310) representative of a target tissue (e.g., the object 105). For example, the image data frames are received from an ultrasound imaging component (e.g., the transducer array 112). For example, the image data frames include per-channel data (e.g., the data 312) corresponding to acoustic elements of the ultrasound imaging component.

At step 720, the method 700 includes determining a delay profile (e.g., the delay profile 412) for the ultrasound imaging component in relation to the target tissue based on the plurality of image data frames. For example, the delay profile includes a time-shift value for each channel. In an embodiment, a single delay profile may be determined from the image data frames, where time-shift values are computed to time-align the per-channel data across the channels. In an embodiment, a per-pixel delay profile may be determined from the imaging data frames, where a subset of data is selected for each channel based on a spatial point of interest and time-shift values are computed to time-align the subsets across the channels.

At step 730, the method 700 includes determining a phase aberration correction configuration (e.g., the configuration 332) for a sequence of one or more shear wave pulses (e.g., the shear wave pulses 304) based on the delay profile. The phase aberration correction configuration may include beamforming delays for generating and/or receiving the sequence of one or more shear wave pulses.

At step 740, the method 700 includes transmitting the beamforming delays to the ultrasound imaging components for generation and/or reception of one or more shear wave pulses.

Aspects of the present disclosure can provide several benefits. For example, the calibration or determination of delay profiles to account for the acoustic characteristics of underlying tissue structures can correct the root cause of focusing errors in ultrasound SWE. The real-time determination of the delay profiles based on high-frame rate B-mode imaging pulses can provide accurate estimates of the acoustic characteristics. The real-time pre-compensation of phase aberration during push and/or tracking pulse generation and/or the real-time post-compensation of phase aberration during the tracking pulse reception can provide aberration-free SWE data. Thus, the disclosed embodiments can provide improve ultrasound SWE performance. The disclosed embodiments can be applied to any tissue structure in a patient body. The disclosed embodiments are suitable for any diagnosis requiring tissue viscoelasticity information.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging system, comprising:
an interface circuit coupled to an ultrasound imaging component, the interface circuit arranged to receive a plurality of image data frames, wherein the plurality of image data frames are representative of a target tissue; and
a processing circuit in communication with the interface circuit,
wherein the processing circuit is arranged to determine a delay profile for the ultrasound imaging component in relation to the target tissue based on the plurality of image data frames,
wherein the processing circuit is arranged to determine a phase aberration correction configuration for a sequence of one or more shear wave pulses based on the delay profile,
wherein the sequence of one or more shear wave pulses is associated with the ultrasound imaging component and a stiffness measure of the target tissue, and
wherein the sequence of one or more shear wave pulses comprises a push pulse.

2. The ultrasound imaging system of claim 1,
wherein the ultrasound imaging component comprises a plurality of transducer elements,
wherein the plurality of image data frames include brightness-mode (B-mode) data from a plurality of channels, the plurality of channels corresponding to the plurality of transducer elements,
wherein the delay profile includes time-shift values for the plurality of channels.

3. The ultrasound imaging system of claim 2, wherein the processing circuit is arranged to determine the delay profile by determining a time-shift value for each of the plurality of channels so as to time-align the B-mode data across the plurality of channels.

4. The ultrasound imaging system of claim 2, wherein the processing circuit is arranged to determine the delay profile by,
selecting a subset of the B-mode data from each of the plurality of channels based on a spatial point of interest, and
determining a time-shift value for each of the plurality of channels to time-align the subsets of the B-mode data across the plurality of channels.

5. The ultrasound imaging system of claim 2, wherein the processing circuit is arranged to determine the phase aberration correction configuration by determining beamforming delays for at least one of a generation or a reception of the sequence of one or more shear wave pulses by the plurality of transducer elements.

6. The ultrasound imaging system of claim 1,
wherein the processing circuit is arranged determine a motion measure associated with the target tissue based on the plurality of image data frames,
wherein the processing circuit is arranged to select a subset of the plurality of image data frames based on the motion measure,
wherein the processing circuit is arranged to determine the delay profile based on the subset of the plurality image data frames.

7. The ultrasound imaging system of claim 1, wherein the sequence of one or more shear wave pulses further comprises a transmit tracking pulse after the push pulse and a receive tracking pulse after the transmit tracking pulse.

8. The ultrasound imaging system of claim 1, wherein the interface circuit is arranged to transmit the phase aberration correction configuration to the ultrasound imaging component.

9. The ultrasound imaging system of claim 1,
wherein the interface circuit is arranged to receive response data from the ultrasound imaging component,
wherein the response data is associated with the sequence of one or more shear wave pulses in relation to the target tissue,
wherein the processing circuit is arranged to determine the stiffness measure of the target tissue based on at least the response data.

10. The ultrasound imaging system of claim 9, further comprising a display in communication with the processing circuit, wherein the display is arranged to display a confidence map associated with the stiffness measure of the target tissue.

11. The ultrasound imaging system of claim 1, further comprising a user input interface arranged to receive a selection for an automatic phase aberration correction, wherein the processing circuit is arranged to determine the phase aberration correction configuration based on the selection.

12. The ultrasound imaging system of claim 1, further comprising an ultrasound imaging probe, the ultrasound imaging probe comprising:
the ultrasound imaging component;
the processing circuit; and
a display arranged to display a confidence map associated with the stiffness measure of the target tissue.

13. A method of ultrasound imaging diagnostic, comprising:
receiving, from an ultrasound imaging component, a plurality of image data frames representative of a target tissue;
determining a delay profile for the ultrasound imaging component in relation to the target tissue based on the plurality of image data frames; and
determining a phase aberration correction configuration for a sequence of one or more shear wave pulses based on the delay profile, the sequence of one or more shear wave pulses associated with the ultrasound imaging component and a stiffness measure of the target tissue, wherein the sequence of one or more shear wave pulses comprises a push pulse.

14. The method of claim 13,
wherein the ultrasound imaging component comprises a plurality of transducer elements,
wherein the plurality of image data frames include brightness-mode (B-mode) data from a plurality of channels, the plurality of channels corresponding to the plurality of transducer elements of the ultrasound imaging component,
wherein the delay profile includes time-shift values for the plurality of channels.

15. The method of claim 14, wherein the determining the delay profile includes determining a time-shift value for each of the plurality of channels to time-align the B-mode data across the plurality of channels.

16. The method of claim 14, wherein the determining the delay profile includes:
selecting a subset of the B-mode data from each of the plurality of channels based on a spatial point of interest; and
determining a time-shift value for each of the plurality of channels to time-align the subsets of the B-mode data across the plurality of channels.

17. The method of claim 14,
wherein the determining the phase aberration correction configuration includes determining beamforming delays for at least one of a generation or a reception of the sequence of one or more shear wave pulses by the plurality of transducer elements of the ultrasound imaging component,
wherein the method includes transmitting the phase aberration correction configuration to the ultrasound imaging component.

18. The method of claim 13, further comprising:
determining a motion measure associated with the target tissue based on the plurality of image data frames;
selecting a subset of the plurality of image data frames based on the motion measure; and
determining the delay profile based on the subset of the plurality image data frames.

19. The method of claim 13, further comprising:
receiving, from the ultrasound imaging component, response data associated with the sequence of one or more shear wave pulses in relation to the target tissue; and
determining the stiffness measure of the target tissue based on at least the response data.

20. The method of claim 19, further comprising displaying a confidence map associated with the stiffness measure of the target tissue.

* * * * *